United States Patent
O'Connell et al.

(10) Patent No.: US 10,426,652 B2
(45) Date of Patent: Oct. 1, 2019

(54) NASAL DILATOR

(71) Applicant: Nasal Medical Limited, Dublin (IE)

(72) Inventors: Martin O'Connell, Tralee (IE); Keith Yeager, Jersey City, NJ (US)

(73) Assignee: Nasal Medical Limited, Dublin (IE)

( * ) Notice: Subject to any disclaimer, the term of this patent is extended or adjusted under 35 U.S.C. 154(b) by 0 days.

(21) Appl. No.: 15/271,803

(22) Filed: Sep. 21, 2016

(65) Prior Publication Data

US 2017/0027736 A1 Feb. 2, 2017

Related U.S. Application Data

(63) Continuation of application No. PCT/US2015/021787, filed on Mar. 20, 2015.

(60) Provisional application No. 61/968,798, filed on Mar. 21, 2014.

(51) Int. Cl.
| | |
|---|---|
| *A62B 23/06* | (2006.01) |
| *A61F 5/08* | (2006.01) |
| *A61M 29/00* | (2006.01) |

(52) U.S. Cl.
CPC .............. *A61F 5/08* (2013.01); *A61M 29/00* (2013.01); *A62B 23/06* (2013.01)

(58) Field of Classification Search
CPC ... A61F 5/08; A61F 5/56; A61F 2/186; A61K 9/0043; A61M 29/00; A61M 15/08; A61M 15/085; A62B 23/06
USPC ........................................................ D24/135
See application file for complete search history.

(56) References Cited

U.S. PATENT DOCUMENTS

| | | | |
|---|---|---|---|
| 4,201,217 A | 5/1980 | Slater | |
| 4,221,217 A * | 9/1980 | Amezcua | A62B 23/06 128/203.22 |
| 2010/0030252 A1 | 2/2010 | Stewart | |
| 2011/0125091 A1* | 5/2011 | Abbate | A61F 2/186 604/96.01 |
| 2012/0125340 A1* | 5/2012 | Chou | A61M 16/105 128/206.11 |
| 2012/0279504 A1* | 11/2012 | Moore | A62B 23/06 128/206.11 |

FOREIGN PATENT DOCUMENTS

NL          1010730 C2    6/2000

OTHER PUBLICATIONS

European Patent Search Report for European Application No. 15765915.2, dated Sep. 19, 2017, 9 pages.

* cited by examiner

*Primary Examiner* — Peter S Vasat

(57) ABSTRACT

A nasal apparatus which is placed in a nostril in order to provide several respiratory benefits includes a nasal insert having a hub, a plurality of arched legs, and a lateral face. Each of the plurality of arched legs comprises a proximal end and a free end positioned opposite each other, wherein the proximal end is adjacently connected to the hub. The plurality of arched legs is positioned around the hub forming a nasal shell structure in the shape of an inner nasal surface of the nostril, wherein the nasal insert is flexible as to apply pressure to the inner nasal surface. The nasal apparatus may further include a bridge and a subsequent nasal insert, wherein the bridge is adjacently connected to both the nasal insert and the subsequent nasal insert, and is positioned in between the nasal insert and the subsequent nasal insert.

14 Claims, 4 Drawing Sheets

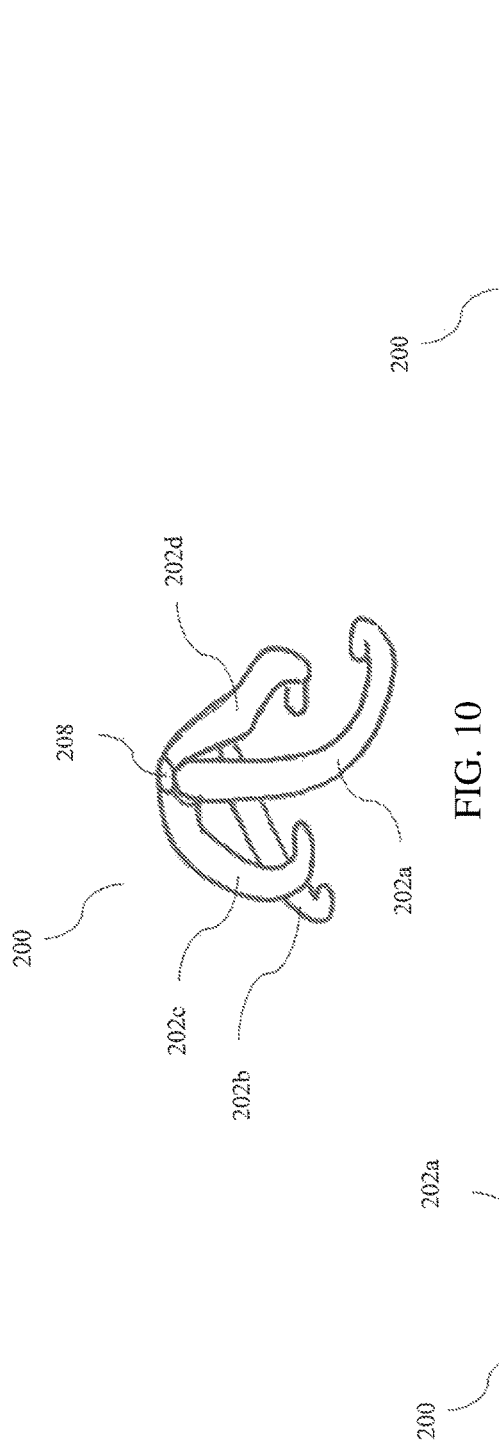
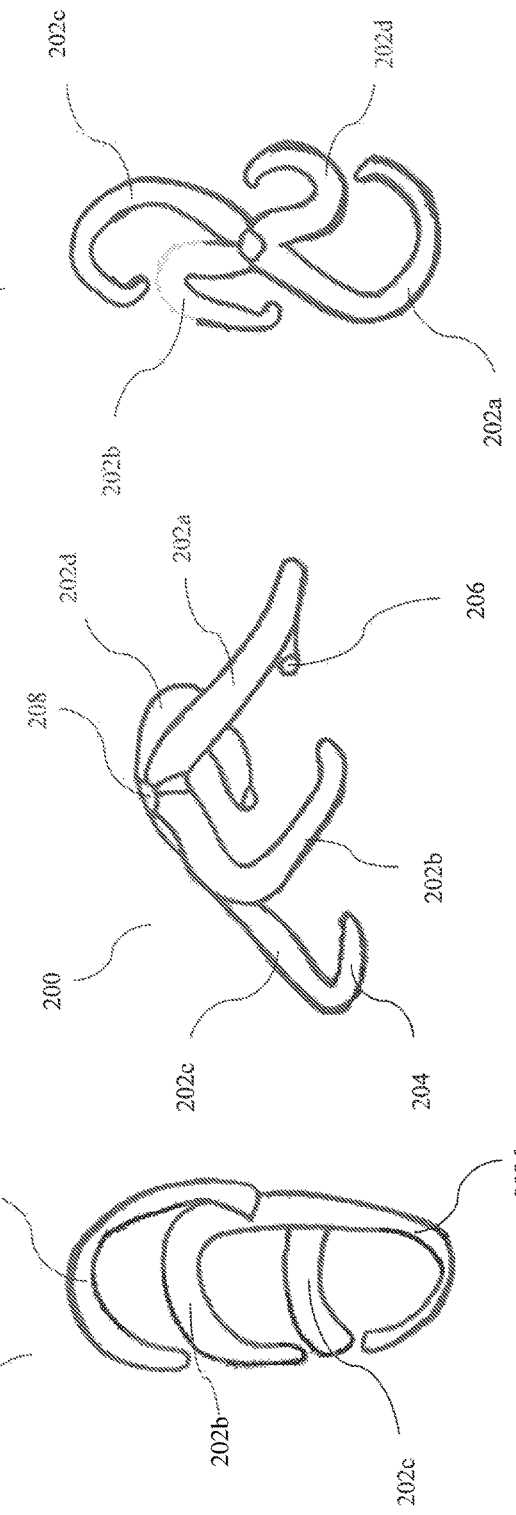
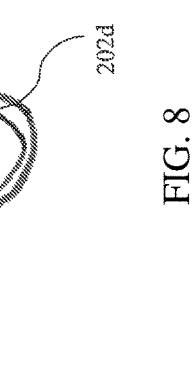

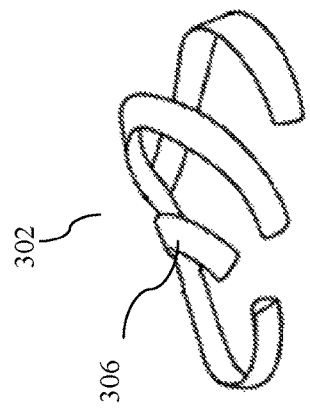
FIG. 16
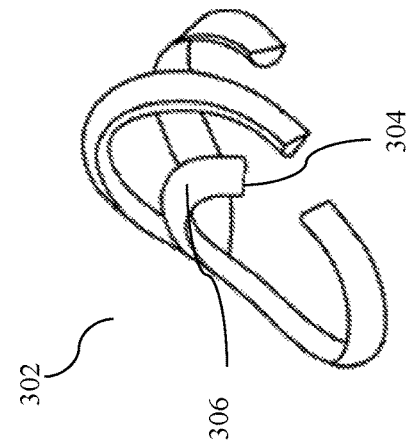
FIG. 15
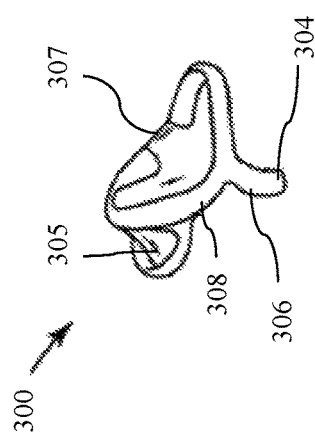
FIG. 14
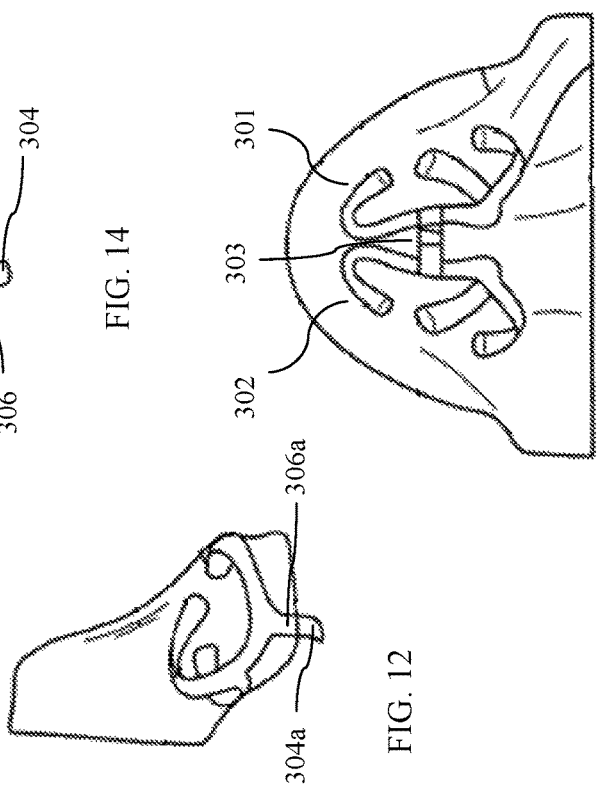
FIG. 13
FIG. 12

NASAL DILATOR

CROSS REFERENCE TO RELATED APPLICATION

The current application is a continuation of PCT Patent Application Ser. No. PCTIUS2015/021787, filed Mar. 20, 2015, which claims priority to U.S. Provisional Patent Application Ser. No. 61/968,798, filed Mar. 21, 2014, the disclosures of which are hereby incorporated by reference.

FIELD OF THE INVENTION

The present invention relates generally to a nasal apparatus which improves respiration by expanding the nasal airways and potentially providing a filter to block irritating or harmful particles.

BACKGROUND OF THE INVENTION

Respiratory issues result from a number of conditions, ranging from comparatively simple ones like congestion to more difficult ones like sleep apnea. To address these concerns, a number of products have been developed. Generally, these products are chemical based (e.g. sprays and medicine) or structural based (dilators and filters); the present invention concerns itself with the latter grouping. Placed in a person's nostrils, such devices improve breathing by expanding the nasal airways and filtering out foreign bodies which normally irritate and agitate a person's nose. The present invention improves upon these basic principles by providing an apparatus which can be used with or without a filter. The filter can be readily incorporated into the design via insert-molding, adhesive, or welding (thermal or ultrasonic). Furthermore, the apparatus is adaptable to different nostril sizes unlike many existing products which must be sold in different sizes to accommodate individual differences.

The present invention has an anatomic design influenced by 3D morphology. Existing products are simple geometries or only based on the 2D profile of the nasal opening, and are often closed profile which limits their ability to conform to a wide range of nostril sizes. The present invention is modeled on the 3D surfaces of the nasal geometry and incorporates features for maintaining a comfortable fit for a wide range of size variation from one user to the next. The current drawings show a device suitable for Type I & II nostril types, and alternate orientations of the device can be manufactured with proportions suitable for Type III & V, for Type VI & VII, and for Type IV.

Greater range of nostril size variation within a Type set, for example set I & II, is achieved by incorporating individual arms which allow flexibility in key anatomic locations. The length of the arms and the nature of the open profile design allow the device to conform to the individual user's nostril. The profile cross section of the arm (generally oval shaped) is designed to allow bending along its thin dimension, while maintaining a relatively larger area of contact in its long dimension. The larger area of contact, thin bending profile, and long beam length reduce the pressure applied by the device when inserted into a relatively smaller nostril.

The profile is anatomically influenced, and has three arms. They merge on the medial side of the nostril and form the largest contact area at the septal cartilage, which is relatively planar. One arm extends in the anterior direction, following the structure of the majar alar cartilage. A second arm extends in the posterior direction and follows the curvature of the alar fibrofatty tissue structure. A third arm extends superior and arcs around to an inferior orientation, terminating near the posterior portion of the majar alar cartilage. The three arms serve to dilate the nasal cavity by acting on these structures. The flexibility of the device within and between each arm is primarily in the medial/lateral direction, and secondarily in the anterior/posterior direction. While one configuration of the present invention is described with three arms, a fourth arm may also be included for additional locational stability The present invention acts to reduce respiratory exposure to viruses, allergens, germs, flu's, colds, bacteria, molds, dust, pet dander, pollen, pollutants, contaminants, second hand smoke, carcinogens, and other airborne contaminants. The present invention also acts to improve sleeping by increasing nasal airflow and mitigating or eliminating snoring, headaches, and nausea. An additional benefit of the present invention is increased oxygen intake and nitric oxide production, desirable to persons who want to enhance their athletic performance.

BRIEF DESCRIPTION OF THE DRAWINGS

FIG. 8 is a bottom plan view of the alternative embodiment having an anatomic design and an additional leg.

FIG. 9 is a perspective view of the yet another alternative embodiment having an anatomic design, wherein the arched legs spiral.

FIG. 10 is a front view of the alternative embodiment having an anatomic design, wherein the arched legs spiral.

FIG. 11 is a top plan view of the alternative embodiment having an anatomic design, wherein the arched legs spiral.

FIG. 12 is a perspective view of the alternative embodiment having an anatomic design being positioned within a nostril and having a bridge.

FIG. 13 is a perspective view of the alternative embodiment having an anatomic design being positioned within nostrils wherein the nasal insert is connected to a subsequent nasal insert by the bridge.

FIG. 14 is a perspective view of the alternative embodiment having an anatomic design, wherein a filter is connected to the nasal insert.

FIG. 15 is a perspective view of another alternative embodiment having an anatomic design, wherein an additional leg is attached to the hub.

FIG. 16 is a right side view of the alternative embodiment having an anatomic design and an additional leg.

DETAILED DESCRIPTION OF THE INVENTION

All illustrations of the drawings are for the purpose of describing selected versions of the present invention and are not intended to limit the scope of the present invention.

Figure 1:
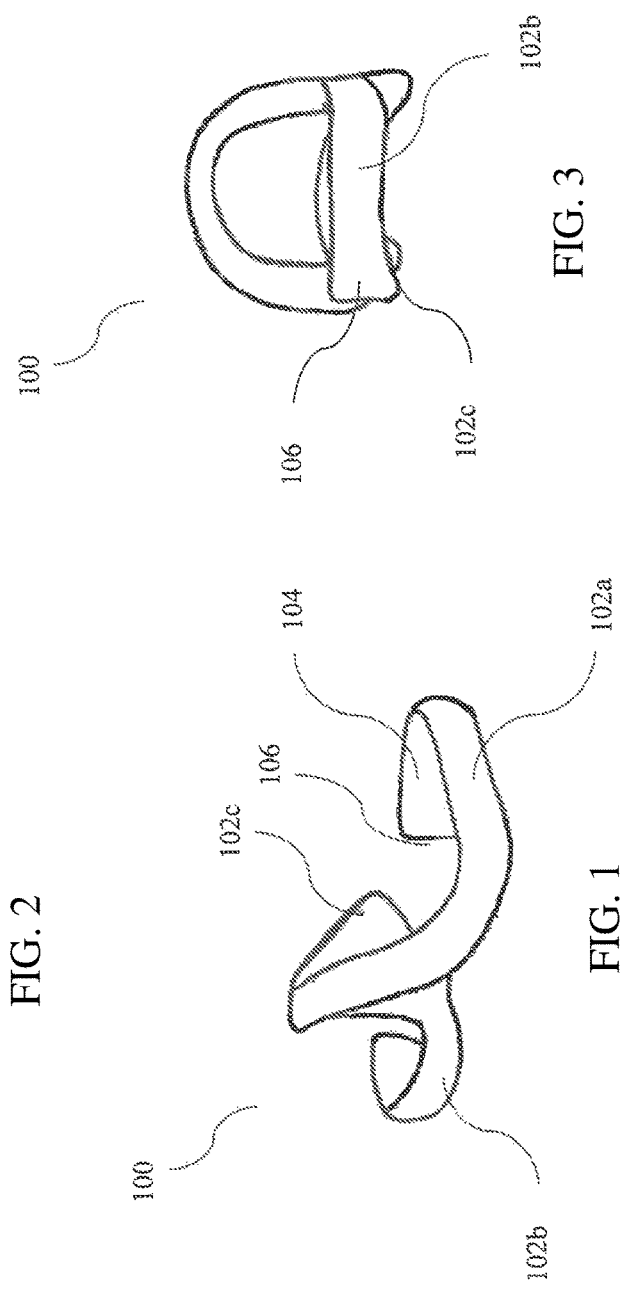
FIG. 1 is a perspective view of an alternative embodiment of the present invention having an anatomic design influenced by 3D morphology.
Figure 2:
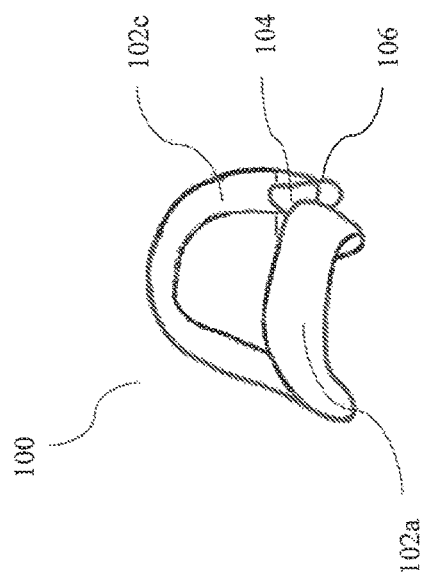
FIG. 2 is a front elevational view of the alternative embodiment having an anatomic design.
Figure 3:
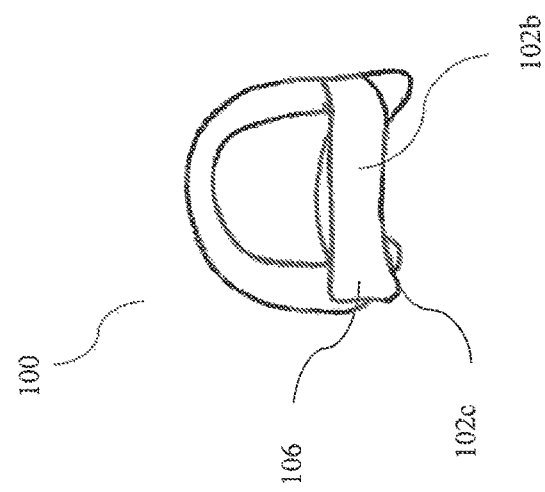
FIG. 3 is a rear elevational view of the alternative embodiment having an anatomic design.
Figure 5:
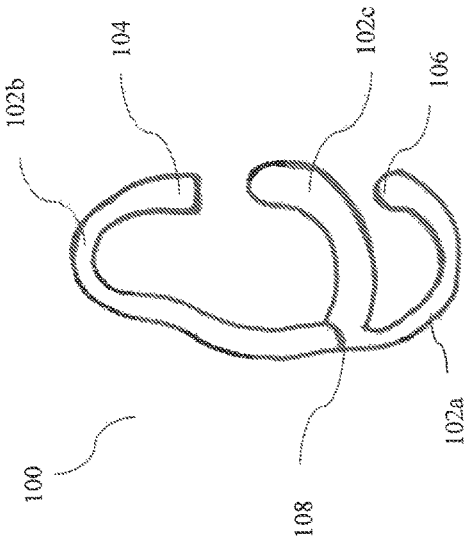
FIG. 5 is a left side elevational view of the alternative embodiment having an anatomic design.
Figure 4:
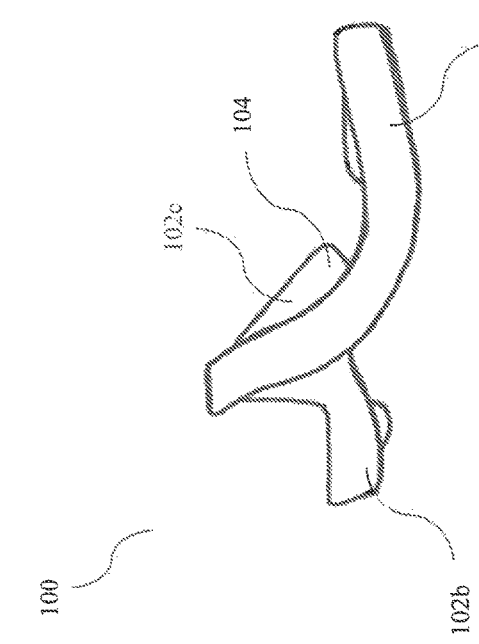
FIG. 4 is a right side elevational view of the alternative embodiment having an anatomic design.
Figure 7:
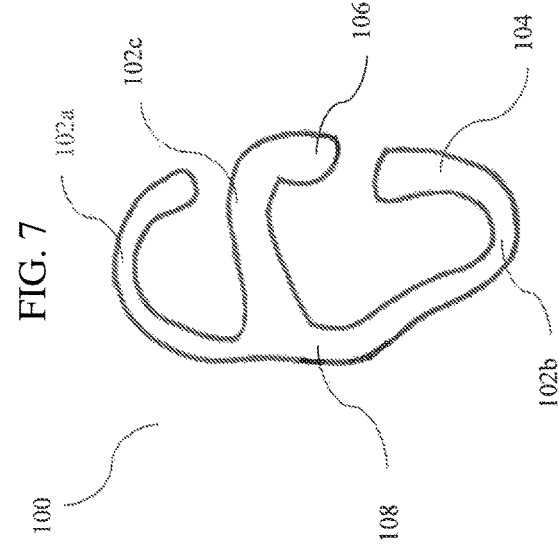
FIG. 7 is a bottom plan view of the alternative embodiment having an anatomic design.
Figure 6:
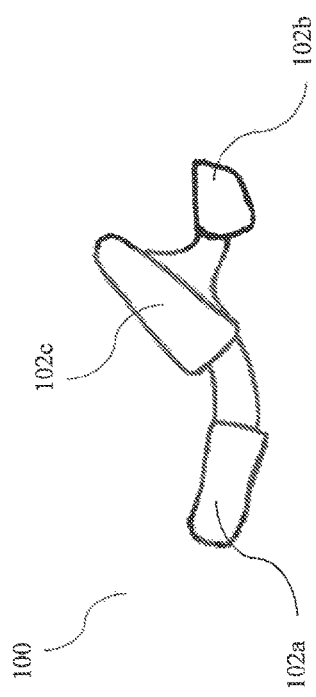
FIG. 6 is a top plan view of the alternative embodiment having an anatomic design.

The present invention is a nasal apparatus which is placed in the nostril in order to provide several respiratory benefits. An insert of the present invention comprises a hub and a plurality of arched legs, with the plurality of arched legs being connected around the hub. The plurality of arched legs, in combination with the hub, give the present invention an elliptical dome-shaped appearance. Each of the plurality of arched legs comprises a free end. When inserted into a nostril, the free end of each of the plurality of arched legs presses against the interior surface. A resulting opposing force pushes the connected hub in the opposite direction, causing the nostril to expand due to the forces of the plurality of arched legs and the hub. This configuration and resulting nostril expansion is a core aspect of the present invention, as the increased airway enhances breathing and mitigates related issues such as snoring. The insert, with and without filter, is illustrated in FIG. 1-FIG. 16.

FIGS. 1-6 show device 100 according to an embodiment having an anatomic design. According to an embodiment, device 100 may comprise legs 102a, 102b, and 102c. Greater range of nostril size variation is achieved by incorporating the plurality of arched legs 102 which allow flexibility in key anatomic locations. The length of the each of the plurality of arched legs 102, and the nature of the open profile design of device 100 allow the device 100 to conform to the individual user's nostril. The profile cross section of each leg 102 (generally oval shaped) is designed to allow bending along its thin dimension, while maintaining a relatively larger area of contact in its long dimension. The larger area of contact, thin bending profile, and long beam length reduce the pressure applied by the device when inserted into a relatively smaller nostril.

The free end 106 of each of the plurality of arched legs 102 comprises a foot 104. Foot 104 is preferably arc shaped and provides a greater surface area which can disperse pressure across with the nostril interior and thus provide a more comfortable experience for a user. Preferably, also in the interest of ergonomics, the edge of each foot 104 is smooth and rounded.

According to an alternative embodiment depicted in FIGS. 9-11, device 200 may comprise legs 202a, 202b, 202c, and 202d. According to an embodiment the plurality of arched legs comprises a first leg 202a, a second leg 202b, a third leg 202c, and a fourth leg 202d, each of which are flexible bars that are radially positioned around hub 208. Legs 202 are equally spaced around hub 208 such that each that the free end 206 of any given leg 202 is separated by an imaginary 90 degree arc of an imaginary circle, the center of which is positioned on hub 208 and the perimeter of which intersects each free end 206.

According to an embodiment shown in FIGS. 9-11, a pair of legs 202 is designed to orient along an axis running from the apex of the nose to the back of the nose and a second pair of legs 202 along a perpendicular medial axis. The first leg 202a and the third leg 202c are positioned opposite each other around hub 208, forming the first pair of legs which is oriented into the nostril beginning at the apex of the nose. The second leg 202b and the fourth leg 202d are similarly positioned opposite each other around hub 208, forming the second pair of legs which is oriented along the medial axis.

The geometric shape of the legs themselves can vary with different embodiments, examples of which are provided in FIGS. 1-8. While FIG. 1-FIG. 4 depict an embodiment 100 with a curved pattern of legs (seen as such when viewed along the axis of the hub). In an alternative embodiment, FIGS. 9-11 depict how a spiral pattern of legs can be used instead. It is noted that in both embodiments 100 and 200 respectively, the free ends 104, 204 of the legs 102, 202 are positioned in a somewhat circular pattern with equal arcs separating each free end 104, 204, which essentially maintains the orientations of each pair of legs.

A spiral embodiment 200 comprises a central hub 208, as clearly illustrated in FIG. 9-11. According to an embodiment, a spiral embodiment 200 may comprise four legs 202a-202d as depicted in FIGS. 9-11. According to an embodiment, a primary advantage of a spiral embodiment 200 is that a spiral embodiment 200 is easier to place In reference to FIGS. 1-8, in an alternative embodiment of the present invention, the profile of the present invention may be anatomically influenced, and has three legs 102a, 102b, and 102c. Legs 102 merge on the medial side of the nostril and form the largest contact area at the septal cartilage, which is relatively planar. One leg 102a extends in the anterior direction, following the structure of the majar alar cartilage. A second leg 102b extends in the posterior direction and follows the curvature of the alar fibrofatty tissue structure. A third leg 102c extends superior and arcs around to an inferior orientation, terminating near the posterior portion of the majar alar cartilage. The three legs 102a, 102b, and 102c serve to dilate the nasal cavity by acting on these structures. The flexibility of the device within and between each leg 102 is primarily in the medial/lateral direction, and secondarily in the anterior/posterior direction. In an alternative embodiment of FIG. 8, a fourth leg may also be included for additional locational stability.

According to an embodiment, the free end 104 of the first leg 102a, which is positioned adjacent to the nostril opening when in use, comprises a tab. This tab, an elongated section foot 104, is perpendicular to the arc of the corresponding foot and oriented along the same apex-rear axis as the first pair of legs 102. This tab provides an easily accessed handle that allows a user to pull the present invention out of the nostril for removal. When the present invention is properly inserted into a nostril tab is similarly positioned within the nostril and out of sight of other persons.

Turning now to FIGS. 8-11, in an alternative embodiment of the present invention, foot 204 of the second leg 202b, the third leg 202c, and the fourth leg 202d is molded at an angle. As a result, each foot 204 comprises a lateral face which presses against the nasal walls (rather than the nasal floor as with the preferred embodiment).

The nasal apparatus 100 and 200 as heretofore described is provided for a single nostril. Preferably, as depicted in FIGS. 12-16, according to an embodiment the present invention is distributed in pairs, with an insert provided for each nostril. These pairs can be completely independent from each other such that they may easily be inserted or removed individually. Alternatively, a left nostril insert 301 and a right nostril insert 302 can be connected by a bridge 303 which is connected to each nostril at the foot 304 of the first leg 306a. Bridge 303 is a thin strip of material which rests against the columella of the nose; this positioning minimizes exposure of the bridge and places it such that it is mostly obscured and unassuming without directed observation. The intention is for bridge 303 to be essentially hidden such that it may be worn throughout the day without attracted undesired attention to a user. The visibility of the flexible bridge 303 can be further reduced or eliminated in various ways. One non-limiting example is using a translucent or transparent material for the bridge construction. Other ways of hiding or obscuring bridge 303, when included, can be utilized in other embodiments. To provide more flexibility to a user of the present invention, bridge 303 can be removably attached to each insert 301 and 302; this allows a user the choice of using bridge 303 for better structure or removing bridge 303 for better aesthetics or comfort. A user can even alter between using bridge 303 and not as their personal preferences or situational circumstances change.

In addition to insert 300, the present invention may further comprise a separate attachable filter piece 305 as depicted in FIG. 14. Filter 305 can be readily incorporated into the design via insert-molding, adhesive, or welding (thermal or ultrasonic). If adapted for user with filter 305, the insert 300 further comprises a perimeter 307 that intersects the foot 304 of each leg 306 and is positioned around the center of insert 300. The perimeter 307 is preferably elliptical in shape to match the three-dimensional shape of insert 300. Perimeter 307 acts as a rim-mounting surface, preferably made of a silicone material to help retain an attached filter 305. Expanding upon the improved respiratory benefits, attachable filter 305 is provided to mitigate allergens, dust particles, and other foreign bodies which might agitate or disrupt a person's nasal airways and breathing. Filter 305 is shaped to fit over insert 300, sharing the same general dome shape. The apex of filter 305 is positioned atop the center of hub 308 while perimeter 307 of filter 305 is positioned around the plurality of legs 302, adjacent to each foot 304 of legs 306. Preferably, perimeter 307 of filter 305 comprises an adhesive coating to help secure filter 305 to rim 307 of insert 300. Filter 305 is attached to insert 300 through molding, in which an injection mold of the insert body is created around insert 300. The insert body 300 is permeated in several sections to allow for a secure attachment of filter 305 via adhesive insert molding. The attachment process can utilize a variety of methods, such as ultrasonic welding or hot joining, to complete the attachment of filter 305 to insert 300.

To use the present invention, a user places a nasal insert in each nostril such that the first leg 306a and associated foot 304a are positioned adjacent to the nostril opening, the hub 308 of insert 300 is positioned adjacent to the roof of the nostril, and the feet 304 of insert 300 are positioned on the floor of the nostril. Once placed inside the nostril, insert 300 presses against the interior nostril surfaces such that the airways is expanded. To conform insert 300 to the nostril, a user can press on the exterior of their nose, causing insert 300 to take a shape matching the nostril interior. The applied force acting upon insert 300 (via the nostril wall) causes insert 300 to flatten and compress, enabled by its elastic and flexible construction. This allows insert 300 to better adapt to the interior of the nose while still increasing expanding the airway. Furthermore, in embodiment 300 which may include a filter 305, the combination of filter 305 and insert 300 create a seal with respect to the nasal cavity, which prevents the flow of air from circumventing filter 305.

The elastic and flexible construction of insert 300 is especially beneficial as they allow for a better range of fits with a single model size. There are a wide variety of individual characteristics which mean that what one person considers a good or comfortable fit may be poorly suited to another. Such differences are not limited across people, as a person's features are not perfectly symmetrical and their individual left and right nostrils can vary in size. Correct sizing is important with regards to nostrils, as devices which are too big are very uncomfortable while devices which are too small are not secure and less effective. The present invention overcomes these limitations, as insert 300 compresses and flexes to conform to a user's individual nostril. As a result, the present invention is adaptable to individual variations in nostril size and shape, providing a "one size fits all" solution.

The compressive forces applied to insert 300 by the nose and the plurality of legs 302 help keep the inserts 300 inside the nostril during regular everyday activities. The present invention 300 is, minus bridge 303 when used, internally secured and not visible in normal situations. When a user wishes to remove inserts 300 and filters 305, such as for removal or replacement, they can simply apply pressure to the tip of the nose. Pressure should be applied in an upward direction and in a direction opposite of the nostril the insert is being removed from. Thus, to remove insert 300 from the left nostril pressure is applied upwards and the tip of the nose is moved to the right, while to remove insert 300 from the right nostril the tip of the nose is instead moved to the left. This results in further compression of the insert, which assumes a flatter shape. As insert 300 flattens, foot 304 which is normally positioned adjacent to the nostril opening is moved out of the nostril, providing an easily gripped handle. This exposed foot 304 makes it simple for a user to grasp and remove insert 300.

According to an embodiment, filter 305 and insert 300 are preferably made in dark colors which do not contrast the interior of the nose and thus are effectively invisible to outside viewpoints. It is noted that when the present invention both utilizes bridge 303 and is made from a single mold, the bridge 303 and inserts 300 must be made from the same material; in this scenario bridge 303 and inserts 300 are made of a transparent or translucent material to better hide bridge 303. This is comparison to a bridgeless embodiment in which inserts 300 are made in a dark color. The filter itself can vary in several aspects, the most notable of which is the fineness of the filtering medium. In a preferred embodiment the filter prevents passage of particles that large than 0.1 microns and smaller than 100 microns in size. This range has been selected as filters 305, which are finer than a tenth of a micron may inhibit airflow and breathing, while a filter that allows passage to particles larger than one hundred microns may prove ineffective against a number of potential allergens and other irritating foreign bodies.

Ideally, filter 305 prevents passage of harmful or irritating particles including but not limited to bacteria, viruses, pathogens, allergens, dust, pollen, pollutants, toxins, carcinogens, and airborne particles capable of causing disease.

Although the invention has been explained in relation to its preferred embodiment, it is to be understood that many other possible modifications and variations can be made without departing from the spirit and scope of the invention.

We claim:

1. A nasal apparatus comprising:
  a plurality of arched, flexible legs wherein:
    a) each of the plurality of arched, flexible legs comprises a proximal end and a free end;
    b) a first leg, a second leg, and a third leg, and wherein the three legs merge on the medial side of the nostril forming a large surface area for contacting the septal cartilage, when the apparatus is inserted into the nostril(s);
    c) the proximal end and free end are opposite ends of the same leg;
    d) the free end of each of the plurality of arched flexible legs comprises an enlarged foot providing an expanded lateral face for contacting a lateral surface of the inner nostril, the expanded lateral face of the enlarged foot is designed to apply pressure against an inner nasal surface of a nostril, when the nasal apparatus is positioned in the nostril
    e) the nasal apparatus is flexible and applies pressure to the inner nasal surface of the nostril when the nasal apparatus is positioned within the nostril, thereby holding the nasal apparatus within the nostril(s);

f) the plurality of arched legs allows flexibility in key anatomic locations, the profile cross section of the leg being configured to allow bending along its thin dimension, while maintaining a relatively large area of contact in its long dimension, so as to conform to an individual user's nostril(s); and g) the first leg is configured to extend in an anterior direction, following the structure of the majar alar cartilage of the nostril;

h) the second leg is configured to extend in a posterior direction, following the curvature of an alar fibro-fatty tissue structure; and i) the third leg is configured to extend in a superior direction, and then to arc around to an inferior orientation, terminating near a posterior portion of the majar alar cartilage.

2. The nasal apparatus of claim 1, comprising a pair of nasal apparatus conjoined by a bridge, where the bridge provides a mechanism to protect against inserting the nasal apparatus too far into the nostril(s), while also serving as a mechanism for removing the nasal apparatus from the nostril(s).

3. The conjoined nasal apparatus of claim 2, wherein the bridge is removably attached to each nasal apparatus of the pair.

4. The nasal apparatus of claim 2, wherein the bridge connecting the conjoined pair of nasal apparatus is formed of a translucent or transparent material.

5. The nasal apparatus of claim 1 comprising:
a filter, the filter being attached to the nasal apparatus and wherein the perimeter of the filter is positioned around the plurality of arched legs, adjacent to the free end of each of the plurality of arched legs.

6. The nasal apparatus of claim 5, wherein the filter is attached to the nasal apparatus through a molding process, where an injection mold of the body of the nasal apparatus is created around the nasal apparatus.

7. The nasal apparatus of claim 6, wherein the filter is incorporated into the nasal insert via insert-molding, adhesive, or thermal or ultrasonic welding.

8. The nasal apparatus of claim 5 wherein:
a) the nasal apparatus comprises a rim;
b) the filter comprises an adhesive coating;
c) the rim intersects the free end of each of the plurality of arched legs; and
d) the filter is secured to the rim via an adhesive coating.

9. The nasal apparatus of claim 8, wherein the rim is elliptical in shape.

10. The nasal apparatus of claim 8, wherein the perimeter of the filter comprises an adhesive to secure the filter to the rim.

11. The nasal apparatus of claim 8, wherein the rim comprises a silicone material to aid retention of an attached filter.

12. The nasal apparatus of claim 8, wherein the perimeter of the filter is positioned around the plurality of legs, and adjacent to each of the free ends of the legs.

13. The nasal apparatus of claim 1, wherein the enlarged foot is molded at an angle.

14. The nasal apparatus of claim 1, wherein the edge of each enlarged foot is smooth and rounded.

* * * * *